United States Patent [19]

Schwertfeger

[11] 4,401,829
[45] Aug. 30, 1983

[54] PROCESS FOR THE PREPARATION OF PERFLUORINATED CARBOXYLIC ACID FLUORIDES

[75] Inventor: Werner Schwertfeger, Butzbach, Fed. Rep. of Germany

[73] Assignee: Hoechst Aktiengesellschaft, Frankfurt am Main, Fed. Rep. of Germany

[21] Appl. No.: 300,920

[22] Filed: Sep. 10, 1981

[30] Foreign Application Priority Data

Sep. 12, 1980 [DE] Fed. Rep. of Germany ....... 3034549

[51] Int. Cl.³ .......................................... C07C 67/317
[52] U.S. Cl. .................................. 560/180; 560/190; 560/192; 260/544 F
[58] Field of Search ............... 560/180, 182, 192, 190; 260/544 F

[56] References Cited

PUBLICATIONS

Knunyants, I. L. et al., Translation of Izvestiya Akademii Nauk SSSR, Seriya Khimicheskaya, No. 12, pp. 2725–2730, Apr. 13, 1973, Translation by Consultants Bureau, a Div. of Plenum Publ. Corp., (pp. 2659–2662).
Lustig, Max et al., *Inorganic Chemistry*, vol. 3, (1964), pp. 287–288.
Lustig, Max et al., *Inorganic Chemistry, vol. 4, (1965), pp. 1441–1443.*

*Primary Examiner*—Natalie Trousof
*Assistant Examiner*—L. Hendriksen

*Attorney, Agent, or Firm*—Curtis, Morris & Safford

[57] ABSTRACT

Perfluorinated carboxylic acid fluorides which also have an ester group in the molecule are prepared by decomposition of perfluorinated fluorosulfato compounds of the formula I

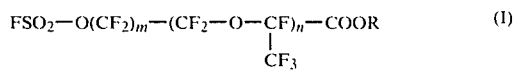

$$FSO_2-O(CF_2)_m-(CF_2-O-CF)_n-COOR \quad\quad (I)$$
$$\phantom{FSO_2-O(CF_2)_m-(CF_2-O-}|$$
$$\phantom{FSO_2-O(CF_2)_m-(CF_2-O-}CF_3$$

in which R = alkyl, aryl or aralkyl with preferably up to 10 C atoms, in particular $CH_3$ or $C_2H_5$, m = an integer from 1 to 10, preferably 1 to 8 and in particular 1 to 6, and n = 0 or an integer from 1 to 10, preferably 0 to 3 or in particular 0 or 1, in the presence of catalytic amounts of at least one alkali metal fluoride and in the absence of solvents; the compounds have the formula II

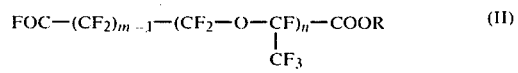

$$FOC-(CF_2)_{m-1}-(CF_2-O-CF)_n-COOR \quad\quad (II)$$
$$\phantom{FOC-(CF_2)_{m-1}-(CF_2-O-}|$$
$$\phantom{FOC-(CF_2)_{m-1}-(CF_2-O-}CF_3$$

in which R, m and n have the same meaning as in formula I.

The compounds II are valuable intermediates, in particular for the preparation of perfluorinated vinyl compounds, which can in turn be processed to homopolymers and copolymers which are exceptionally stable to chemicals or heat.

10 Claims, No Drawings

PROCESS FOR THE PREPARATION OF PERFLUORINATED CARBOXYLIC ACID FLUORIDES

Perfluorinated carboxylic acid fluorides are primarily intermediates in organic fluorine chemistry. If they contain the structural unit

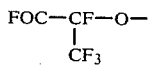

they can, for example, be converted directly into perfluorinated vinyl compounds by pyrolysis:

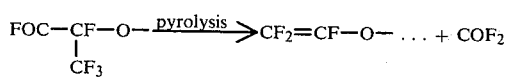

If the said structural unit is not present, it can be produced, for example, by reaction of the perfluorinated carboxylic acid fluoride with hexafluoropropene epoxide in a known manner:

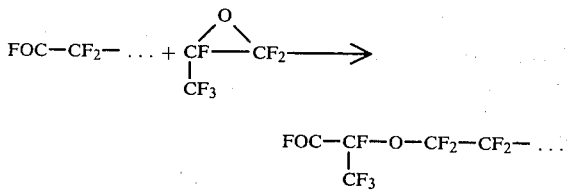

The perfluorinated organic vinyl compounds can be converted into valuable oligomers and polymers which are exceptionally stable to chemicals and heat by homopolymerization and copolymerization. The oligomers with a liquid consistency are used, for example, as lubricants and anti-friction agents and as hydraulic fluids, and the polymers with a solid consistency are used, inter alia, as coating materials, elastomers, ion exchangers (if basic or acid groups are also present) and the like, and in particular in all cases where particular emphasis is placed on resistance to chemicals and heat.

Examples of perfluorinated carboxylic acid fluorides which also contain another functional group in the molecule are perfluorinated dicarboxylic acid fluoride-esters. The ester group can then be converted, for example, into the free acid group in the customary manner, so that perfluorinated dicarboxylic acid fluoride-esters are particularly suitable as starting materials and intermediates for the preparation of perfluorinated ion exchangers.

Numerous perfluorinated dicarboxylic acid fluoride-esters and processes for their preparation are already known. For example, such perfluorinated dicarboxylic acid fluoride-esters are obtained by the process described in German Offenlegungsschrift No. 2,651,531 by reaction of perfluorolactones with an alcohol:

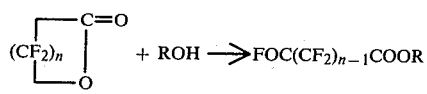

R=alkyl
n=an integer from 2 to 4

However, the applicability of this process is very limited since only perfluorobutyrolactone (n=3) is accessible on an industrial scale, and in particular either from $I(CF_2)_3COF$ (German Auslegeschrift No. 2,642,824) or from $I(CF_2)_4I$ (German Auslegeschrift No. 2,635,312), and in the latter case only as a mixture with large amounts of perfluorotetrahydrofuran and with perfluorosuccinic acid difluoride, which can scarcely be separated off from the lactone by distillation.

In the process of German Offenlegungsschrift No. 2,708,677, the starting materials are perfluorinated dicarboxylic acid fluoride-esters of the formula:

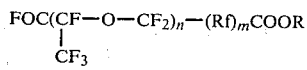

in which R=alkyl, Rf=a bifunctional ($C_1$-$C_{10}$)-perfluoro group, m=0 or 1 and n=a number from 1 to 5; the corresponding carboxylate-esters are prepared therefrom by reaction with an alkali metal carbonate, and perfluorinated vinyl compounds are then prepared from these esters by pyrolysis:

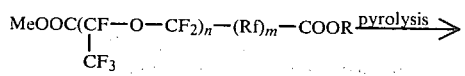

(Me = alkali metal)

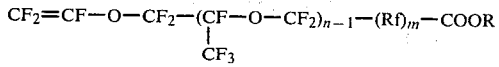

Perfluorinated dicarboxylic acid fluoride-esters of the formula:

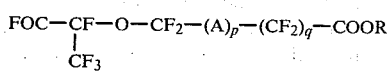

in which A=a bifunctional ($C_1$-$C_{10}$)-perfluoro group, R=an organic group, p=0 or 1 and q=a number from 1 to 8, are known from German Offenlegungsschrift 2,751,050; they are prepared by reacting the corresponding perfluorinated dicarboxylic acid difluorides with alcohol.

However, this process does not proceed selectively to give the perfluorinated dicarboxylic acid fluoride-esters, but always leads to mixtures containing the isomeric half-esters and the diesters which are difficult to separate off and can together make up to about 30% of the mixture and cannot be used for the preparation of the perfluorinated vinyl compounds.

German Offenlegungsschrift 2,817,366 describes perfluorinated dicarboxylic acid fluoride-esters of the following formula:

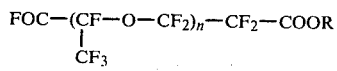

in which R=($C_1$-$C_6$)-alkyl and n=a number from 0 to 6. The compounds are prepared as follows:

if n = 0: $R^1O-CF_2-CF_2-COOR \xrightarrow{SO_3}$ ($R^1 = C_1-C_6$—alkyl)

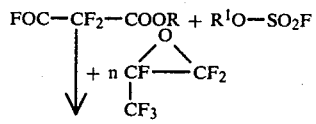

if n = 1-6:

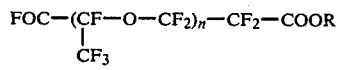

This process is of practical importance only with the starting compound $CH_3O-CF_2-CF_2-COOCH_3$. The $CH_3OSO_2F$ which is formed therefrom as a by-product in the stoichiometric amount during the reaction with $SO_3$ is a highly toxic compound, the dangerousness of which is comparable to that of dimethyl sulfate and similar methylating agents [Alder, R. W. et al., Chem. Eng. News 56, 37, 56 (1978)].

The acid fluoride group can also be produced in perfluorinated organic compounds by decomposition of the fluorosulfato group in the presence of alkali metal fluorides.

The decomposition of a primary fluorosulfate with KF is described in Inorg. Chem. 3 287 (1964).

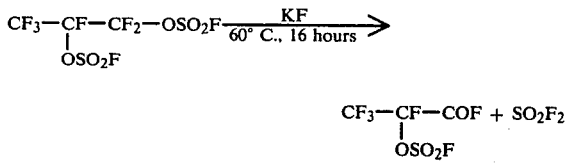

No amounts are given. All the other examples set forth in this reference show either complete destruction of the starting compound or complete recovery of the fluorosulfate employed.

In Inorg. Chem. 4 1441 (1965), primary fluorosulfates are reacted with an approximately 50 molar excess of KF per mole of fluorosulfate.

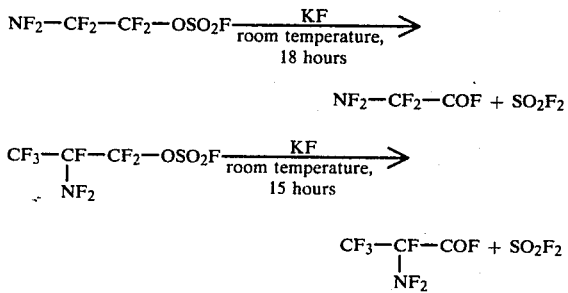

J. Fluorine Chem. 14 519 (1979) describes the reaction of primary fluorosulfates with cesium fluoride.

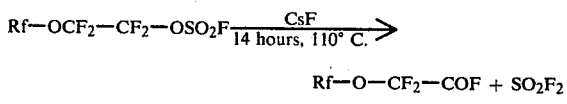

$Rf = CF_3$ or $SF_5$

The fluorosulfate and the CsF are employed in this reaction in a molar ratio of 1:20.

It is a common factor of all these reactions that they are carried out without a solvent. In these cases, a considerable excess of alkali metal fluoride appears necessary for the reaction to take place.

Izv. Akad. Nauk SSSR, Ser. Khim. 1973 2659 (English edition) showed that catalytic amounts of alkali metal fluoride can also be used for such reactions if an aprotic polar solvent, such as diglyme or acetonitrile, is employed:

$$CF_3-CO-CF_2OSO_2F \xrightarrow[\text{solvent}]{KF} CF_3-CO-COF + SO_2F_2$$

Our own experiments showed that the reaction of ω-fluorosulfatoperfluorocarboxylic acid esters with catalytic amounts of an alkali metal fluoride in the presence of a solvent, such as tetraglyme, does not lead to the expected perfluorodicarboxylic acid fluoride-esters, but gives perfluorodicarboxylic acid difluoride and perfluorodicarboxylic acid diesters, in addition to complete decomposition of the starting material (see the comparison example).

On the basis of this finding and of the abovementioned examples from the literature for splitting primary fluorosulfates, it was thus surprising that ω-fluorosulfatoperfluorocarboxylic acid esters can be converted into perfluorodicarboxylic acid fluoride-esters in a high yield in the presence of catalytic amounts of an alkali metal fluoride and in the absence of an aprotic polar solvent.

The invention relates to a process for the preparation of perfluorinated carboxylic acid fluorides by decomposition of perfluorinated fluorosulfato compounds in the presence of at least one alkali metal fluoride, which comprises using, as the perfluorinated fluorosulfato compounds, compounds of the formula I $$FSO_2-O(CF_2)_m-(CF_2-O-CF)_n-COOR \quad (I)$$
$$\qquad\qquad\qquad\qquad\qquad\quad | $$
$$\qquad\qquad\qquad\qquad\qquad CF_3$$

in which R=alkyl, aryl or aralkyl with preferably up to 10 C atoms, in particular $CH_3$ or $C_2H_5$, m=an integer from 1 to 10, preferably 1 to 8 and in particular 1 to 6, and n=0 or an integer from 1 to 10, preferably 0 to 3 or in particular 0 or 1, and carrying out the decomposition in the presence of only catalytic amounts of an alkali metal fluoride and in the absence of aprotic polar solvents.

The perfluorinated carboxylic acid fluorides which also have an ester group in the molecule, of the formula II:

$$FOC-(CF_2)_{m-1}-(CF_2-O-CF)_n-COOR \quad (II)$$
$$\qquad\qquad\qquad\qquad\qquad\qquad |$$
$$\qquad\qquad\qquad\qquad\qquad\quad CF_3$$

in which R, m and n have the same meaning as in formula I, are thus formed in high yields from the compounds I.

The starting compounds I for the process according to the invention are particularly advantageously prepared by the process of co-pending patent application U.S. Ser. No. 300,945 filed on the same day, which process comprises (a) electrolyzing ω-H-perfluorocarboxylic acid halides of the formula III:

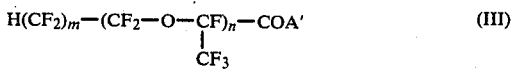

H(CF$_2$)$_m$—(CF$_2$—O—CF)$_n$—COA'  (III)
　　　　　　　　　|
　　　　　　　　　CF$_3$ in which m and n have the same meaning as in the formulae I and II and A'=halogen, in an electrolyte consisting of a mixture of fluorosulfonic acid FSO$_3$H and one of its alkali metal salts, using metals of the platinum group (osmium, iridium or platinum) and/or glassy carbon as the anode material and a cathode material which is customary, but stable under the electrolysis conditions, isolating the ω-fluorosulfato-perfluorocarboxylic acid halides thereby formed, of the formula IV

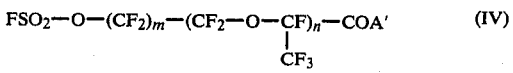

FSO$_2$—O—(CF$_2$)$_m$—(CF$_2$—O—CF)$_n$—COA'  (IV)
　　　　　　　　　　　　　　　|
　　　　　　　　　　　　　　　CF$_3$ in which m and n again have the same meaning as in the formulae I and II and A' has the same meaning as in formula III, and (b) esterifying these compounds with an organic hydroxy compound of the formula V

ROH  (V)

in which R has the meaning given in the case of formula I, to give ω-fluorosulfato-perfluorocarboxylic acid esters of the formula I.

The alkali metal fluorides (LiF, NaF, KF, RbF and CsF) are catalysts for the process according to the invention.

The catalysts can be employed either individually or as a mixture with one another. The amount of catalyst is in general between about 1 and 50 mole %, preferably between about 10 and 30 mole %, relative to the starting compound I.

The reaction is carried out without the addition of an aprotic polar solvent, and particularly advantageously without any solvent.

The reaction temperatures are in general in the range between about −20° and +120° C., depending on the catalyst used.

The reaction can be carried out either under normal pressure or under increased pressure.

The sequence in which the reactants are brought together is practically of no importance for the reaction according to the invention. However, it is advantageous to ensure thorough mixing of the batch throughout the entire period of the reaction by stirring well.

In a preferred embodiment, the catalyst and the fluorosulfate I are brought together and the mixture is heated slowly, until evolution of gas starts. When the evolution of gas has ended, the batch is distilled over a column.

The perfluorinated carboxylic acid fluorides II which also have an ester group in the molecule and are prepared by the process according to the invention are in general colorless liquids which are sensitive to hydrolysis. They are therefore to be prepared in the absence of moisture.

Because of the high yields, which are in most cases over about 90% of theory, and the high purity of the end products II, the invention represents a considerable advance in this field.

The compounds II are chiefly processed by known methods to perfluorinated vinyl compounds which also contain an ester group in the molecule and are in turn converted into valuable homopolymers and copolymers. The homopolymers and copolymers are used, inter alia (after hydrolysis of the ester groups) as ion exchangers which are resistant to chemicals and heat.

The invention will now be illustrated in more detail by the following examples. The examples of the invention (A) are also followed by a comparison example (B), which shows that the reaction according to the invention no longer functions in the presence of solvents.

A. EXAMPLES OF THE INVENTION

EXAMPLE 1

Methoxalyl fluoride CH$_3$OOC—COF

The reaction is carried out in a fume cupboard.

5.8 g (0.1 mole) of dry, finely powdered potassium fluoride and 104 g (0.5 mole) of fluorosulfatodifluoroacetic acid methyl ester are introduced, at room temperature, into a dry flask with a magnetic stirrer, thermometer, reflux condenser and bubble counter. The batch is heated, with good stirring. From an internal temperature of 50° C., sulfuryl fluoride starts to escape. When the evolution of gas has ended, the mixture is heated under reflux for a further hour. Subsequent distillation over a packed column gives 48 g (90.5%) of methoxalyl fluoride with a boiling point of 91° C. (760 mm Hg).

Analysis: Calculated C 33.98, H 2.85, F 17.91. Found C 34.00, H 2.80, F 17.80.

$^1$H-NMR (CDCl$_3$): 4.00 (s)

$^{19}$F-NMR (CDCl$_3$)*: +23.8 (—COF)

IR (neat): 5.35μ (COF), 5.64μ (COO)

*CFCl$_3$ is used as the internal standard in all the $^{19}$F-NMR spectra.

EXAMPLE 2

Carbomethoxydifluoroacetic acid fluoride CH$_3$OOC—CF$_2$—COF

The reaction is carried out in a fume cupboard.

5.8 g (0.1 mole) of dry, finely powdered potassium fluoride and 128 g (0.496 mole) of ω-fluorosulfatoperfluoropropanoic acid ethyl ester are introduced, at room temperature, into a dry flask with a magnetic stirrer, thermometer, reflux condenser and bubble counter. On subsequent heating of the batch, evolution of gas (SO$_2$F$_2$) occurs from an internal temperature of 55° C. When the evolution of gas has ended, the batch is heated under reflux for a further hour. The batch is stirred well throughout the entire reaction. Distillation gives 70 g (90.4%) of carbomethoxydifluoroacetic acid fluoride with a boiling point of 86° C. (760 mm Hg).

Analysis: Calculated C 30.79, H 1.94, F 36.52. Found C 31.05, H 1.95, F 35.60.

$^1$H-NMR (CDCl$_3$): 4.00 (s)

$^{19}$F-NMR (CDCl$_3$): +22.6 (COF, −110.9 (CF$_2$)

IR (gas spectrum): 5.3μ (COF), 5.52μ (—COO—)

EXAMPLE 3

Carboethoxydifluoroacetic acid fluoride C$_2$H$_5$OOC—CF$_2$—COF

The reaction is carried out as described for carbomethoxydifluoroacetic acid fluoride.

5.8 g (0.1 mole) of potassium fluoride and 100 g (0.35 mole) of 3-fluorosulfatoperfluoropropanoic acid ethyl ester are employed. Distillation gives 57 g (95.8%) of carbethoxydifluoroacetic acid fluoride with a boiling point of 98° C. (760 mm Hg).

Analysis: Calculated C 35.31, H 2.96, F 33.51. Found C 35.20, H 3.00, F 33.10.

$^1$H-NMR (CDCl$_3$): 1.40 (t, 3H, J=7 Hz), 4.45 (q, 2H, J=7 Hz)

$^{19}$F-NMR (CDCl$_3$): +22.6 (COF), −111 (CF$_2$)

IR (neat): 5.32 (COF), 5.59 (—COO—)

EXAMPLE 4

4-Carbomethoxyperfluorobutanoic acid fluoride CH$_3$OOC—(CF$_2$)$_3$—COF

The reaction is carried out in a fume cupboard.

78 g (0.21 mole) of 5-fluorosulfatoperfluoropentanoic acid methyl ester and 3.0 g (0.053 mole) of potassium fluoride are introduced into a dry flask with a magnetic stirrer, thermometer, reflux condenser and bubble counter. The batch is heated slowly. Sulfuryl fluoride is liberated from an internal temperature of about 55° C. When the evolution of gas has ended. The reflux condenser is replaced by a packed column with a column head. Distillation gives 49.5 g (88.4%) of 4-carbomethoxyperfluorobutanoic acid fluoride at a boiling point of 117° C. (768 mm Hg).

Analysis: Calculated C 28.14, H 1.18, F 51.93. Found C 28.25, H 1.15, F 51.95.

$^1$H-NMR (CDCl$_3$): 3.97 (s)

$^{19}$F-NMR (CDCl$_3$): +25.44 (1F, COF), −117.9 (4F, CF$_2$), −123.6 (2F, CF$_2$)

IR (neat): 5.33μ (—COF), 5.69μ (—COO—)

EXAMPLE 5

6-Carbomethoxyperfluorohexanoic acid fluoride CH$_3$OOC—CF$_2$—CF$_2$—CF$_2$—CF$_2$—CF$_2$—COF The reaction is carried out in a fume cupboard.

25 g (0.005 mole) of 7-fluorosulfatoperfluoroheptanoic acid methyl ester and 0.6 g (0.01 mol) of potassium fluoride are introduced into a dry flask which is provided with a magnetic stirrer, thermometer, Vigreux column, column head and subsequent cold trap (−78° C.). The batch is heated slowly. Evolution of gas starts from an internal temperature of about 60° C. When the evolution of gas has ended, the mixture is heated for distillation. 15.6 (80%) of 6-carbomethoxyperfluorohexanoic acid fluoride are obtained at a boiling point of 150°–151° C. (746 nm).

Analysis: Calculated C 26.98, H 0.85, F 58.69. Found C 26.7, H 0.8, F 57.9.

$^1$H-NMR (CDCl$_3$): 3.89 (s)

$^{19}$F-NMR (CDCl$_3$): +25.2 (1F, COF), −118.6 (4F, —CF$_2$—COOCH$_3$ and —CF$_2$—CO—), −121.6 (2F, CF$_2$), −123.0 (4F, 2XCF$_2$), IR (neat): 5.30μ (—COF), 5.59μ (—COO—)

EXAMPLE 6

7-Carbomethoxy-6-oxaperfluorooctanoic acid fluoride

The reaction is carried out in a fume cupboard.

96 g (0.18 mole) of 8-fluorosulfatoperfluoro-2-methyl-3-oxa-octanoic acid methyl ester and 5.2 g (0.09 mole) of finely powdered dry potassium fluoride are introduced into a dry flask with a magnetic stirrer, thermometer, reflux condenser and bubble counter. On warming the mixture, evolution of gas starts from an internal temperature of about 60° C. When the evolution of gas has ended, the mixture is heated to 80°–90° C for a further hour. Subsequent distillation over a packed column gives 71 g (93%) of the acid fluoride with a boiling point of 50° C. (12 mm Hg).

Analysis: Calculated C 25.16, H 0.72, F 58.51. Found C 25.50, H 0.70, F 58.80.

$^1$H-NMR (CDCl$_3$)=3.95 (s)

$^{19}$F-NMR (CDCl$_3$): =+27.5 (COF), −78.1 (1F, —O—CF$_2$—, Jgem=148 Hz), −81.6 (CF$_3$), −85.5 (1F, —O—CF$_2$—, Jgem=148 Hz), −118.3 (—CF$_2$—CO—), −122.8 (CF$_2$), −124.9 (CF$_2$), −130.2 (CF)

IR (neat): 5.32μ (COF), 5.59μ (—COO—)

B. COMPARISON EXAMPLE

The reaction is carried out in a fume cupboard.

7.5 g (0.05 mole) of cesium fluoride and 50 ml of tetraglyme are initially introduced, at room temperature, into a dry flask with a magnetic stirrer, thermometer, dropping funnel, Vigreux column, column head and bubble counter. 56 g (0.156 mole) of 5-fluorosulfatoperfluorobutanoic acid methyl ester are added dropwise. Evolution of gas starts immediately. The batch becomes warm. It is then heated, for distillation. During this procedure, slight evolution of gas can also be observed. The IR spectrum of the gas given off shows that, inter alia, CO$_2$, SO$_2$F$_2$ and acid fluoride(s) are present. Distillation gives 8.5 g of a liquid which has a boiling point of 40°–50° C. and, according to the IR spectrum, consists of impure perfluoropentanedicarboxylic acid difluoride. No 4-carbomethoxyperfluorobutanoic acid fluoride is obtained. Perfluoropentanedicarboxylic acid dimethyl ester is detected in the residue by IR spectroscopy.

I claim:

1. A process for the preparation of a perfluorinated carboxylic acid fluoride compound which comprises decomposition of a perfluorinated fluorosulfato compound of the formula

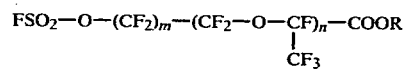

wherein R is alkyl, aryl or aralkyl having 1 to 10 carbon atoms, m is a number from 1 to 10, and n is a number from 0 to 10, said decomposition being conducted at a temperature of about −20° C. to 120° C. in the presence of a catalytically effective amount of from 1 to 50 mole %, relative to said fluorosulfato compound, of an alkali metal fluoride and in the absence of a solvent.

2. The process of claim 1 wherein said alkali metal fluoride is present in an amount of 10 to 30 mole %, relative to said fluorosulfato compound.

3. The process of claim 1 wherein R is CH$_3$.

4. The process of claim 1 wherein R is C$_2$H$_5$.

5. The process of claim 1 wherein m is a number from 1 to 8.

6. The process of claim 1 wherein m is a number from 1 to 6.

7. The process of claim 1 wherein n is a number from 0 to 3.

8. The process of claim 1 wherein n is 0 or 1.

9. The process of claim 1 wherein said alkali metal fluoride is selected from the group consisting of LiF, NaF, KF, RbF and CsF.

10. The process of claim 1 wherein said alkali metal fluoride is KF.

* * * * *